(12) United States Patent
Yuan et al.

(10) Patent No.: US 9,888,878 B2
(45) Date of Patent: Feb. 13, 2018

(54) INTELLIGENT MONITOR OF ERECTILE FUNCTION

(71) Applicants: Jiuhong Yuan, Chengdu (CN); Feng Qin, Chengdu (CN)

(72) Inventors: Jiuhong Yuan, Chengdu (CN); Feng Qin, Chengdu (CN)

(*) Notice: Subject to any disclaimer, the term of this patent is extended or adjusted under 35 U.S.C. 154(b) by 260 days.

(21) Appl. No.: 14/991,916

(22) Filed: Jan. 9, 2016

(65) Prior Publication Data
US 2016/0198993 A1    Jul. 14, 2016

(30) Foreign Application Priority Data
Jan. 9, 2015  (CN) .......................... 2015 1 0013127

(51) Int. Cl.
*A61B 5/00*      (2006.01)
*A61B 5/107*     (2006.01)
*A61B 5/145*     (2006.01)
*A61B 5/01*      (2006.01)
*A41D 13/12*     (2006.01)

(52) U.S. Cl.
CPC .......... *A61B 5/4393* (2013.01); *A61B 5/6804* (2013.01); *A41D 13/1281* (2013.01); *A61B 5/01* (2013.01); *A61B 5/1073* (2013.01); *A61B 5/1075* (2013.01); *A61B 5/14542* (2013.01)

(58) Field of Classification Search
None
See application file for complete search history.

(56) References Cited

U.S. PATENT DOCUMENTS

| | | | | |
|---|---|---|---|---|
| 4,205,671 A * | 6/1980 | Lassen | ...................... | A61F 5/48 128/886 |
| 6,849,041 B2 * | 2/2005 | Astin | ........................ | A61F 5/40 600/38 |
| 7,959,550 B2 * | 6/2011 | Laniado | .................... | A61F 5/41 600/14 |
| 9,445,747 B2 * | 9/2016 | Rahamim | ............ | A61B 5/1135 |

* cited by examiner

*Primary Examiner* — Brian T Gedeon
(74) *Attorney, Agent, or Firm* — Matthias Scholl, PC; Matthias Scholl

(57) ABSTRACT

An intelligent monitor of erectile function, including a pair of underpants equipped with a mechanical device operating to monitor a penile axial length, a penile radial length, and a penile volume; a temperature detector operating to detect a penile temperature; an oxygen saturation measuring device operating to measure a penile oxygen saturation; an integrated circuit chip operating to receive and process output signals from the mechanical device, the temperature detector, and the oxygen saturation measuring device; and a data storage device. The mechanical device, the temperature detector, and the oxygen saturation measuring device are electrically or electronically connected to the integrated circuit chip. The data storage device is electrically or electronically connected to the integrated circuit chip.

8 Claims, 1 Drawing Sheet

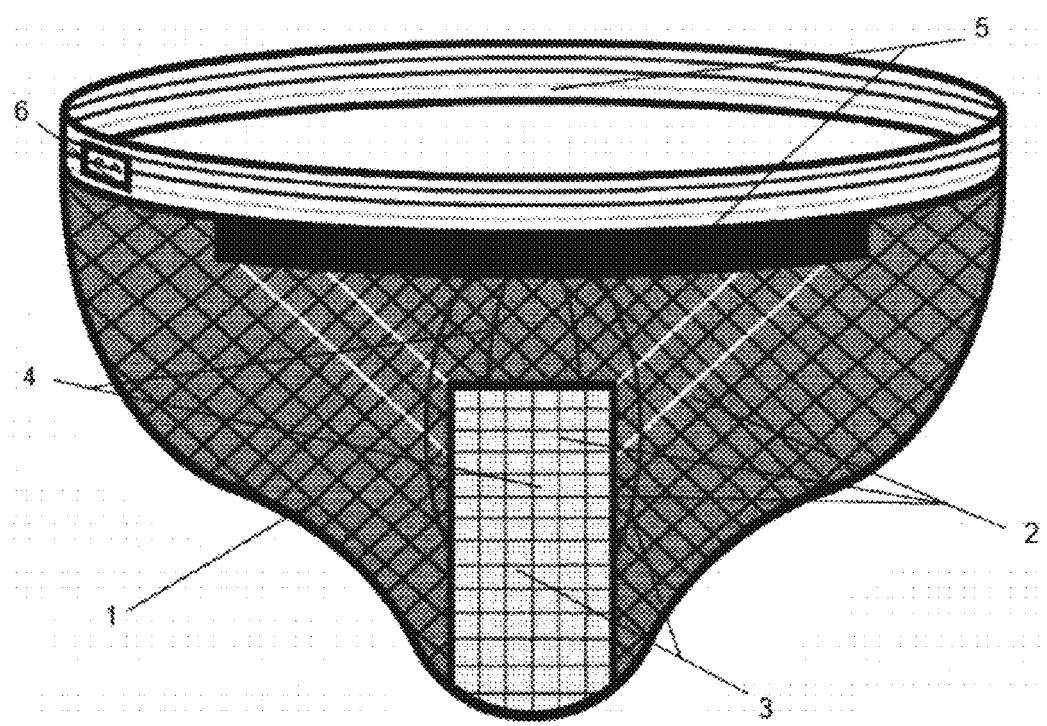

INTELLIGENT MONITOR OF ERECTILE FUNCTION

CROSS-REFERENCE TO RELATED APPLICATIONS

Pursuant to 35 U.S.C. § 119 and the Paris Convention Treaty, this application claims the foreign priority benefit of Chinese Patent Application No. 201510013127.1 filed Jan. 9, 2015, the contents of which, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to an intelligent monitor of erectile function.

Description of the Related Art

Erectile dysfunction (ED) is a common sexual disorder. Penile erection is affected by various factors, including penile structure, blood vessel anatomy, the nervous system, hormonal levels, and sexual arousal.

Depending on the time periods of occurrence, penile erection includes nocturnal tumescence, psychological erection, and reflexive erection. Nocturnal tumescence is not affected by sexual arousal, and hence it can reflect the potential erectile function. Therefore, nocturnal tumescence is used to analyze the cause of ED in clinical application.

The monitoring of the nocturnal penile tumescence is conventionally performed in a sleep laboratory, which requires strict monitoring conditions and is not suitable for clinical application. Several simplified methods are also used for the monitoring of the nocturnal tumescence. The methods include the stamp test method, the pressure belts monitoring method, and the RIGISCAN® method.

The conventional nocturnal tumescence monitoring methods are largely inadequate. For example, the stamp test method is inaccurate. The pressure belts monitoring method can roughly detect the penile rigidity, but it cannot measure the erectile times and quality as well as the penile length and penile diameter. The RIGISCAN® method can detect the parameters including the penile size, the penile rigidity. However, the RIGISCAN® method requires fixed probes and recording devices, and thus causes discomfort. In addition, the RIGISCAN® method gives false negative results when the patient has depression, nightmare, or sleep disorders. Moreover, the RIGISCAN® method cannot measure the axial penile rigidity, is not applicable when the patient has a skin disease or a venereal disease, and is highly costly in application. Therefore, much opportunity for improvement remains.

SUMMARY OF THE INVENTION

In view of the above-described problems, it is one objective of the invention to provide an intelligent monitor of erectile function that comprises a pair of underpants and employs technologies including mechanics, infrared ray, spectrophotometry, and signal conversion to monitor the radial and axial penile rigidity, penile volume, penile temperature, and penile oxygen saturation in real time.

To achieve the above objective, in accordance with one embodiment of the invention, there is provided an intelligent monitor of erectile function, comprising a pair of underpants, the pair of underpants being equipped with a mechanical device, the mechanical device operating to monitor the axial length, the radial length, and the penile volume; a temperature detector, the temperature detector operating to detect the penile temperature; an oxygen saturation measuring device, the oxygen saturation measuring device operating to measure the oxygen saturation in the penile blood vessels; an integrated circuit chip, the integrated circuit chip operating to receive and process output signals from the mechanical device, the temperature detector, and the oxygen saturation measuring device, and the mechanical device, the temperature detector, and the oxygen saturation measuring device being electrically or electronically connected to the integrated circuit chip; and a data storage device, the data storage device being electrically or electronically connected to the integrated circuit chip.

In a class of this embodiment, the mechanical device comprises a deformable fibrous material disposed in the underpants. The deformable fibrous material operates to measure axial and radial penile dimension changes, and the deformable fibrous material deforms as penile size and shape changes. The deformable fibrous material is connected to a tension receptor. The tension receptor is disposed on the inner wall of the underpants. The deformable fibrous material comprises horizontal and vertical macromolecular elastic material, and during penile erection, a corresponding elastic deformation occurs to the elastic material, and then the corresponding tension is converted into an electric signal via the tension receptor. The overall analysis of elastic deformations in different directions can reflect the axial and radial penile rigidity and penile volume changes.

In a class of this embodiment, the tension receptor has a frame-type structure and is disposed on the periphery of the fibrous material. The intelligent monitor has a stable and firm structure, and is unaffected by the erection or postural changes.

In a class of this embodiment, the temperature detector and the oxygen saturation measuring device are embedded in or disposed on the mechanical device, thus ensuring the comfort index of the underpants.

In a class of this embodiment, the temperature detector is an infrared temperature measuring device.

In a class of this embodiment, the data storage device comprises computer memory and a USB interface, and the USB interface is in electric or electronic connection to the computer memory.

In a class of this embodiment, the data storage device comprises a reset button, and the reset button is in electric or electronic connection to the computer memory.

In a class of this embodiment, the integrated circuit chip and the data storage device are disposed on outer wall of the underpants.

In a class of this embodiment, the intelligent monitor further comprises an intelligent terminal comprising a built-in firmware capable of data analysis, data processing, and data imaging, wherein the intelligent terminal exchanges information with the data storage device via the USB interface.

In a class of this embodiment, the intelligent terminal is a computer or mobile phone. Using computer or mobile phone having the built-in firmware as the intelligent terminal will reduce the hardware investment and facilitate popularization.

The working principle of the intelligent monitor is as described below. The radial and axial penile rigidity, penile volume, penile temperature, and penile oxygen saturation are monitored in real time by the mechanical device, the temperature detector, and the oxygen saturation measuring device. The monitored data are converted into an electric signal and output to the integrated circuit chip. The integrated circuit chip analyzes and processes the electric signal and the resulting data are stored in the data storage device. The data storage device transmits the data to the intelligent terminal via the USB interface for analysis, processing and imaging. The data can be cleared using the reset button by a user when required.

Advantages of the intelligent monitor according to embodiments of the invention are summarized as follows: the intelligent monitor comprises devices for monitoring the penile rigidity, penile volume, penile temperature, and penile oxygen saturation, and further comprise a processing system of the monitoring signals. The intelligent monitor can accurately indicate the variations of penile physico-chemical parameters, and it is economic, comfortable, safe, healthy, and convenient for use.

The intelligent monitor of erectile function in this invention is a natural, underpants-type, digital electrometer. The intelligent monitor solves the above mentioned problems, and can collect reliable data for the nocturnal erection in a real and natural sleep state. The intelligent monitor is wireless and convenient for carrying, and can continuously record the radial and axial penile rigidity, penile size, penile temperature, and penile oxygen saturation during night time. Therefore, the intelligent monitor has high operability and practicability.

BRIEF DESCRIPTION OF THE DRAWINGS

The invention is described hereinbelow with reference to accompanying drawings, in which the sole FIGURE is a schematic diagram of an intelligent monitor of erectile function according to one embodiment of the invention.

In the drawings, the following reference numbers are used: 1. Underpants; 2. Mechanical device; 3. Temperature detector; 4. Oxygen saturation measuring device; 5. Integrated circuit chip; 6. Data storage device.

DETAILED DESCRIPTION OF THE EMBODIMENTS

For further illustrating the invention, experiments detailing an intelligent monitor of erectile function are described below. It should be noted that the following examples are intended to describe and not to limit the invention.

Example 1

As shown in the sole FIGURE, the invention provides an intelligent monitor of erectile function comprising a pair of underpants 1. The pair of underpants 1 comprises a mechanical device 2 operating to monitor the axial penile length, the radial penile length, and the penile volume and provide information about the axial penile rigidity, the radial penile rigidity, and the penile volume change. The mechanical device comprises deformable fibrous material. The deformable fibrous material operates to measure axial and radial penile changes, and the deformation degree of the deformable fibrous material changes as penile size and shape changes. The deformable fibrous material is connected to a tension receptor. The tension receptor converts the deformation degree of the deformable fibrous materials into an electric signal. The tension receptor is a frame-type structure and is disposed on the periphery of the deformable fibrous material. The tension receptor is disposed on inner walls of the underpants 1.

The pair of underpants also comprises a temperature detector 3 operating to detect the penile temperature and to provide a penile temperature change. The temperature detector 3 is an infrared temperature measuring device.

The pair of underpants still comprises an oxygen saturation measuring device 4 operating to measure blood oxygen saturation in the penile blood vessels.

The temperature detector 3 and the oxygen saturation measuring device 4 are embedded in or disposed on the mechanical device 2.

The pair of underpants further comprises an integrated circuit chip 5 operating to receive and process output signals from the mechanical device 2, the temperature detector 3, and the oxygen saturation measuring device 4.

The mechanical device 2, the temperature detector 3, and the oxygen saturation measuring device 4 are electrically or electronically connected to the integrated circuit chip 5. The data storage device 5 is electrically or electronically connected to the integrated circuit chip 6. The data storage device 6 comprises a computer memory and a USB interface, and the USB interface is in electric or electronic connection to the memory. The data storage device 6 comprises a reset button, and the reset button is in electric or electronic connection to the memory. The integrated circuit chip 5 and the data storage device 6 are disposed on outer wall of the underpants 1.

The intelligent monitor further comprises an intelligent terminal comprising a built-in firmware capable of data analysis, processing and imaging. The intelligent terminal exchanges information with the data storage device 6 via the USB interface. The intelligent terminal is a computer or mobile phone.

The operational steps of the intelligent monitor are summarized as follows.

Prior to measurement, a patient wears the intelligent monitor of the invention, which is skin-tight and closely clings to the body. The patient lies on his back, and relaxes until his penis is completely limp. When the signal waveform is steady and flat, the patient presses the reset button of the data storage device to zero the mechanical signal. Using the zeroed mechanical signal as a baseline, the subsequent signals are recorded.

In the process of monitoring, the patient can perform his daily activities or sleep as usual. After monitoring, the recorded signals are saved and the recording system is shut off. The USB flash disk is collected for data analysis. The intelligent monitor is taken off by the patient and stored until next use.

The USB flash disk is connected to the intelligent terminal for data analysis, processing, and imaging, and the results are output, and copied or printed for review. During analysis, the influence of the intense activities, the postural change, and etc. to the resulting data (particularly mechanical parameters) should be eliminated.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A monitor of penile erectile function, the monitor comprising:

a) a pair of underpants;
b) a mechanical device, said mechanical device comprising a deformable fibrous material and a tension receptor;
c) a temperature detector;
d) an oxygen saturation measuring device;
e) an integrated circuit chip; and
f) a data storage device;

wherein:
said mechanical device operates to detect a penile axial length, a penile radial length, and a penile volume;
said temperature detector operates to detect a penile temperature;
said oxygen saturation measuring device operates to detect blood oxygen saturation in penile blood vessels;
said integrated circuit chip operates to receive and process output signals from said mechanical device, said temperature detector, and said oxygen saturation measuring device, and output resulting data;
said data storage operates to store said resulting data;
said deformable fibrous material is electrically connected with said tension receptor;
said tension receptor, said temperature detector, said oxygen saturation measuring device are electrically connected with said integrated circuit chip;
said integrated circuit chip is electrically connected with said data storage device;
said temperature detector, said oxygen saturation measuring device are embedded in or disposed on said mechanical device;
said deformable material is disposed in the inner wall of said pair of underpants;
said tension receptor is disposed on the inner wall of said pair of underpants;
said integrated circuit chip and said data storage device are disposed on the outer wall of said pair of underpants;
a deformation degree of said deformable fibrous material corresponds to penile size and shape;
said tension receptor detects tension data corresponding to the deformation degree of said deformable fibrous material; and
said integrated circuit chip processes and analyzes said tension data to provide information about penile axial rigidity, penile radial rigidity, and penile volume change.

2. The monitor of claim 1, wherein:
said deformable fibrous material comprises macromolecular elastic material disposed horizontal with respect to the ground and macromolecular elastic material disposed vertical with respect to the ground;
the deformation degree of said macromolecular elastic material disposed horizontal with respect to the ground corresponds to the penile radial dimension change; and
the deformation degree of said macromolecular elastic material disposed vertical with respect to the ground corresponds to the penile axial dimension change.

3. The monitor of claim 2, wherein said tension receptor is a frame-type structure and is disposed on the periphery of said deformable fibrous material.

4. The monitor of claim 1, wherein said temperature detector is an infrared temperature measuring device.

5. The monitor of claim 1, wherein said data storage device comprises a memory and a USB interface, and said USB interface is in electric or electronic connection with said memory.

6. The monitor of claim 1, wherein said data storage device comprises a reset button, and said reset button is in electric or electronic connection with said memory.

7. The monitor of claim 6, further comprising an intelligent terminal comprising a built-in firmware capable of data analysis, processing and imaging, wherein said intelligent terminal exchanges information with said data storage device via said USB interface.

8. The monitor of claim 7, wherein said intelligent terminal is a computer or a mobile phone.

\* \* \* \* \*